US00PP27701P3

(12) United States Plant Patent
Verschoor

(10) Patent No.: US PP27,701 P3
(45) Date of Patent: Feb. 21, 2017

(54) ***ASTILBE* PLANT NAMED 'VERSRASPBERRY'**

(50) Latin Name: ***Astilbe arendsii*×*Astilbe japonica***
Varietal Denomination: Versraspberry

(71) Applicant: Jan Verschoor, Haarlem (NL)

(72) Inventor: Jan Verschoor, Haarlem (NL)

( * ) Notice: Subject to any disclaimer, the term of this patent is extended or adjusted under 35 U.S.C. 154(b) by 52 days.

(21) Appl. No.: 14/545,487

(22) Filed: May 12, 2015

(65) Prior Publication Data

US 2016/0338250 P1 Nov. 17, 2016

(51) Int. Cl.
*A01H 5/02* (2006.01)

(52) U.S. Cl.
USPC ..... Plt./407

(58) Field of Classification Search
USPC ..... Plt./407
See application file for complete search history.

*Primary Examiner* — Anne Grunberg
(74) *Attorney, Agent, or Firm* — C. A. Whealy

(57) ABSTRACT

A new and distinct cultivar of *Astilbe* plant named 'Versraspberry', characterized by its compact, broadly upright and mounding plant habit; strong and durable leaves; freely and uniformly flowering habit; soft pinkish red purple-colored flowers; and good container and garden performance.

3 Drawing Sheets

Botanical designation: *Astilbe arendsii*×*Astilbe japonica*.
Cultivar denomination: 'VERSRASPBERRY'.

BACKGROUND OF THE INVENTION

The present invention relates to a new and distinct cultivar of *Astilbe*, botanically known as *Astilbe arendsii*×*Astilbe japonica* and hereinafter referred to by the name 'Versraspberry'.

The new *Astilbe* plant is a product of a planned breeding program conducted by the Inventor in Haarlem, The Netherlands. The objective of the breeding program was to create new uniform and freely flowering *Astilbe* plants with attractive leaf and flower coloration.

The new *Astilbe* plant originated from a cross-pollination made by the Inventor in 2007 in Haarlem, The Netherlands, of an unnamed *Astilbe arendsii* seedling selection, not patented, as the female, or seed, parent with an unnamed *Astilbe japonica* seedling selection, not patented, as the male, or pollen, parent. The new *Astilbe* plant was discovered and selected by the Inventor as a single flowering plant from within the progeny of the stated cross-pollination in a controlled greenhouse environment in Haarlem, The Netherlands in 2010.

Asexual reproduction of the new *Astilbe* plant by vegetative divisions in a controlled nursery environment in Heerhugowaard, The Netherlands since the summer of 2010, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Versraspberry'. These characteristics in combination distinguish 'Versraspberry' as a new and distinct *Astilbe* plant:

1. Compact, broadly upright and mounding plant habit.
2. Strong and durable leaves.
3. Freely and uniformly flowering habit.
4. Soft pinkish red purple-colored flowers.
5. Good container and garden performance.

Plants of the new *Astilbe* differ primarily from plants of the parent selections in plant height and flowering habit as plants of the new *Astilbe* are more compact and more freely flowering than plants of the parent selections.

Plants of the new *Astilbe* can be compared to plants of *Astilbe japonica* 'Europa', not patented. In side-by-side comparisons conducted in Haarlem, The Netherlands, plants of the new *Astilbe* and 'Europa' differed in the following characteristics:

1. Plants of the new *Astilbe* were more compact than plants of 'Europa'.
2. Plants of the new *Astilbe* had better container performance than plants of 'Europa'.
3. Plants of the new *Astilbe* were more freely flowering than plants of 'Europa'.
4. Flowers of plants of the new *Astilbe* and 'Europa' differed in flower color as plants of 'Europa' had light pink-colored flowers.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Versraspberry' grown in a container.

The photograph on the second sheet is a close-up view of the upper surface of typical leaves of 'Versraspberry'.

The photograph on the third sheet is a close-up view of typical inflorescences of 'Versraspberry'.

DETAILED BOTANICAL DESCRIPTION

The aforementioned photographs and following observations, measurements and values describe plants grown during the summer in 11-cm containers and in ground beds in an outdoor nursery in Haarlem, The Netherlands and under cultural practices typical of commercial *Astilbe* production. During the production of the plants, day temperatures ranged from 16° C. to 32° C. and night temperatures ranged from 6° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Astilbe arendsii*×*Astilbe japonica* 'Versraspberry'.

Parentage:

*Female, or seed, parent*.—Unnamed *Astilbe arendsii* seedling selection, not patented.

*Male, or pollen, parent*.—Unnamed *Astilbe japonica* seedling selection, not patented.

Propagation:

*Type*.—By vegetative divisions.

*Time to initiate roots*.—About three weeks at 20° C.

*Root description*.—Thick, fleshy; brownish in color.

*Rooting habit*.—Freely branching; dense.

Plant description:

*Plant form and growth habit*.—Herbaceous perennial; compact, broadly upright and mounding plant form with inflorescences held above the foliar plane; flowering stems and leaves basal; freely flowering with numerous basal branches developing per plant, dense and bushy; low vigor to moderately vigorous growth habit; and freely and uniformly flowering habit.

*Growth rate*.—Moderate; from divisions, about 10 months are required to produce fully-grown flowering plants in containers.

*Plant height* (*soil level to top of foliar plane*).—About 17.5 cm.

*Plant height* (*soil level to top of inflorescences*).—About 29.1 cm.

*Plant width* (*spread*).—About 35.6 cm.

*Stem description*.—Length: About 11.4 cm. Diameter: About 4 mm. Internode length: About 3.2 cm. Strength: Strong. Texture: Smooth, glabrous. Luster: Slightly glossy. Color: Close to 144A.

Leaf description:

*Arrangement*.—Alternate; biternately compound; about nine leaflets per leaf.

*Leaf length*(*excluding petiole*).—About 15.4 cm.

*Leaf width*.—About 16.7 cm.

*Leaflet length*.—About 4 cm.

*Leaflet width*.—About 2 cm.

*Leaflet shape*.—Elliptic to ovate.

*Leaflet apex*.—Acute.

*Leaflet base*.—Rounded to short attenuate.

*Leaflet margin*.—Biserrate.

*Leaflet texture, upper and lower surfaces*.—Sparsely to moderately pubescent; rough due to short strigose hairs.

*Leaflet venation pattern*.—Pinnate.

*Leaflet color*.—Developing leaflets, upper surface: Close to 144B. Developing leaflets, lower surface: Close to 146D. Fully expanded leaflets, upper surface: Close to between N137A and 147A; venation, close to 144A. Fully expanded leaflets, lower surface: Slightly lighter than between 146A and 147A; venation, close to 144B.

*Leaf petiole length*.—About 6.7 cm.

*Leaf petiole diameter*.—About 2 mm.

*Leaflet petiole length*.—About 7 mm.

*Leaflet petiole width*.—About 1 mm.

*Leaf and leaflet petiole texture, upper and lower surfaces*.—Smooth, glabrous.

*Leaf and leaflet petiole color, upper surface*.—Close to 146B; at leaflet attachment, close to 176A.

*Leaf and leaflet petiole color, lower surface*.—Close to 144A; at leaflet attachment, close to 176A.

Flower description:

*Flower type and flowering habit*.—Single rotate flowers arranged on terminal panicles; flowers face upright, outward or downward depending on position on the inflorescence; panicles roughly conical in shape; freely and uniformly flowering habit with about 2,750 flowers developing per inflorescence.

*Fragrance*.—Moderately faint; sweet and pleasant.

*Natural flowering season*.—Plants begin flowering about ten months after planting; continuously flowering from early to late summer in The Netherlands.

*Postproduction longevity*.—Flowers last about ten days on the plant; flowers persistent.

*Flower buds*.—Height: About 2 mm. Diameter: About 1 mm. Shape: Ovate. Color: Close to 146C; towards the apex, close to 185A.

*Inflorescence height*.—About 15 cm.

*Inflorescence diameter*.—About 9.3 cm.

*Flower diameter*.—About 5 mm.

*Flower depth*.—About 4 mm.

*Petals*.—Quantity per flower: Typically five in a single whorl. Length: About 3 mm. Lobe width: About 0.75 mm. Shape: Oblanceolate. Apex: Acute. Margin: Entire. Texture, upper and lower surfaces: Smooth, glabrous. Color: Developing petals, upper and lower surfaces: Close to 67B. Fully expanded petals, upper and lower surfaces: Close to 70B; color does not fade with development.

*Sepals*.—Quantity per flower: Typically five in a single whorl, lower 40% of the sepals are fused; campanulate-shaped calyx. Length: About 1.5 mm. Width: About 1 mm. Shape: Ovate. Apex: Acute. Base: Cuneate, fused. Margin: Entire. Texture, upper and lower surfaces: Smooth, glabrous. Color: Developing sepals, upper and lower surfaces: Close to 150B to 150C; margins, close to 181C. Fully expanded sepals, upper and lower surfaces: Close to 150B to 150C; margins, close to 181C.

*Peduncles*.—Length: About 14.1 cm. Diameter: About 3.5 mm. Angle: Primary peduncles are mostly erect; secondary peduncles are about 40° from vertical. Strength: Strong. Texture: Smooth, glabrous. Color: Close to 144A.

*Pedicels*.—Length: About 1 mm. Diameter: About 0.5 mm. Angle: About 50° from peduncle axis. Strength: Moderately strong. Texture: Smooth, glabrous. Color: Close to 150C to 150D.

*Reproductive organs*.—Stamens: Quantity per flower: Typically ten; anthers basifixed. Filament length: About 2.5 mm. Filament color: Close to 70B to 70C. Anther shape: Ovate. Anther length: About 0.5 mm. Anther color: Close to 202B. Pollen amount: Scarce. Pollen color: Close to 156D. Pistils: Quantity per flower: Two. Pistil length: About 1 mm. Stigma shape: Club-shaped. Stigma color: Close to 183B to 183C. Style length: About 0.5 mm. Style color: Close to 70C. Ovary color: Close to 70C.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Additionally, plants of the new *Astilbe* have been observed to be hardy to USDA Hardiness Zone 5.

It is claimed:

1. A new and distinct *Astilbe* plant named 'Versraspberry' as illustrated and described.

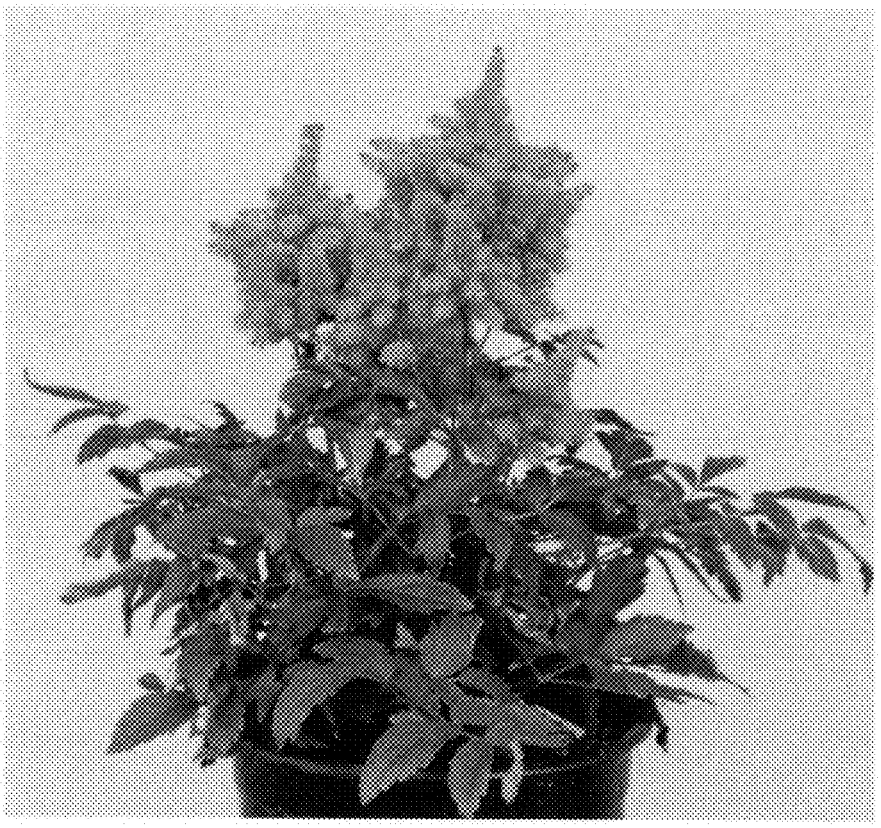

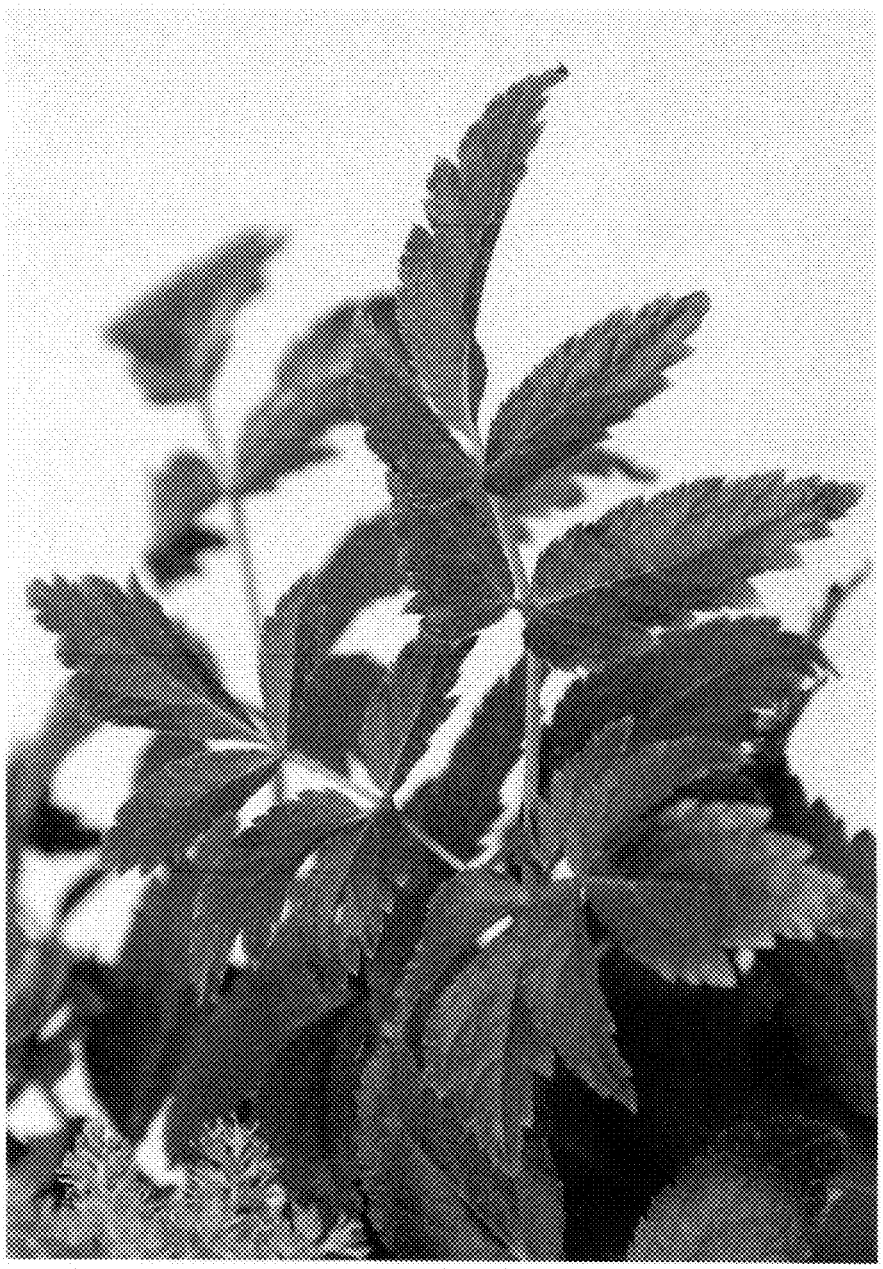

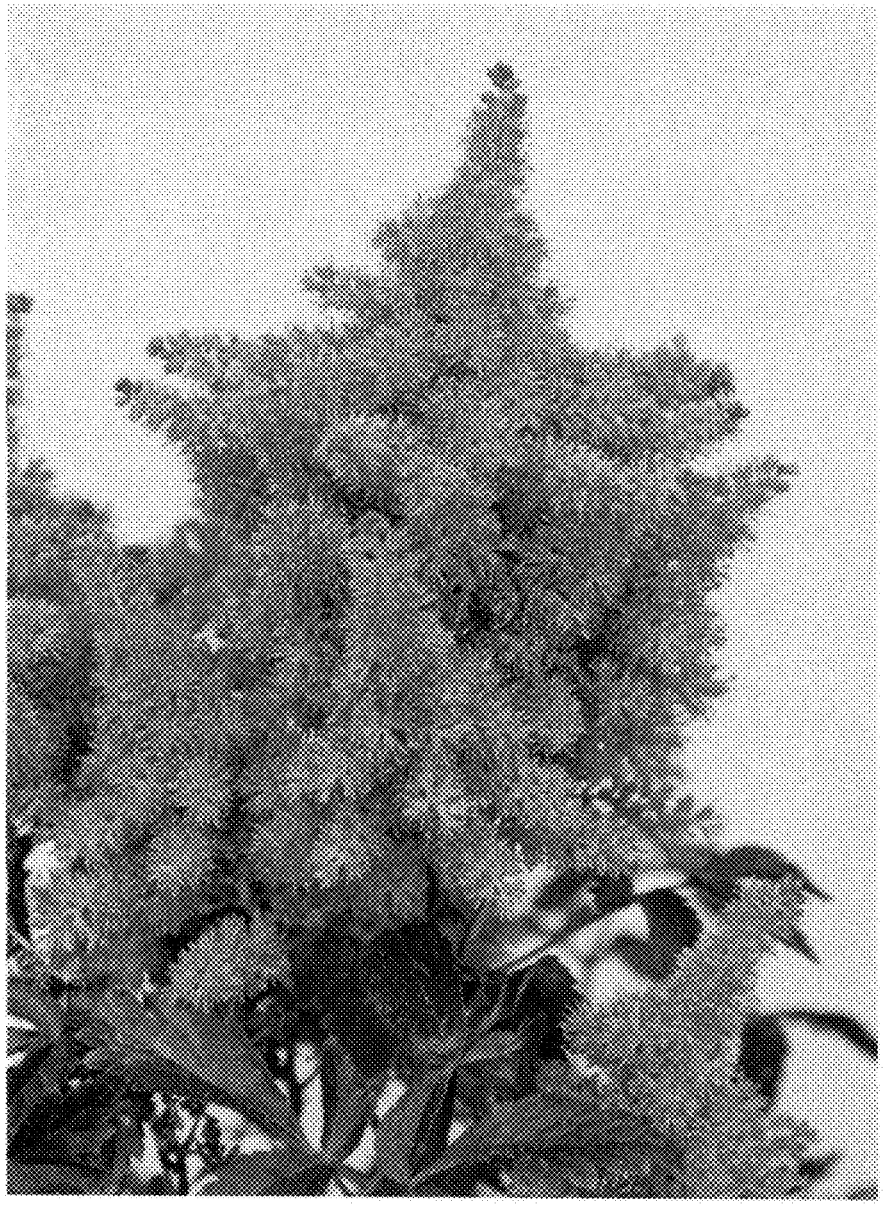

* * * * *